United States Patent
Hillier et al.

(10) Patent No.: US 7,341,989 B2
(45) Date of Patent: Mar. 11, 2008

(54) USE OF LH IN CONTROLLED OVARIAN HYPERSTIMULATION

(75) Inventors: Stephen G. Hillier, Edinburgh (GB); Colin Michael Howles, Geneva (CH)

(73) Assignee: Laboratories Seronosa, Coinsins, Vaud (CH)

( * ) Notice: Subject to any disclaimer, the term of this patent is extended or adjusted under 35 U.S.C. 154(b) by 237 days.

(21) Appl. No.: 10/487,423

(22) PCT Filed: Sep. 12, 2002

(86) PCT No.: PCT/GB02/04147

§ 371 (c)(1), (2), (4) Date: Sep. 14, 2004

(87) PCT Pub. No.: WO03/022301

PCT Pub. Date: Mar. 20, 2003

(65) Prior Publication Data

US 2005/0049199 A1 Mar. 3, 2005

(30) Foreign Application Priority Data

Sep. 12, 2001 (EP) .................................. 01307755

(51) Int. Cl.
*A61K 38/00* (2006.01)
*A61K 38/24* (2006.01)

(52) U.S. Cl. ........................... 514/2; 514/21; 530/313; 530/399

(58) Field of Classification Search ...................... None
See application file for complete search history.

(56) References Cited

U.S. PATENT DOCUMENTS 5,650,390 A 7/1997 Samaritani et al.

FOREIGN PATENT DOCUMENTS

EP 0 170 502 6/1991
WO WO-00/67778 11/2000

OTHER PUBLICATIONS

Rudinger, Peptide Hormones, (Jun. 1976) 1,5-6.*
Richard L. Stouffer and Mary B. Zelinski-Wooten, Overriding follicle selection in controlled ovarian stimulation protocols: Quality vs. quantity, Reproductive Biology and Endocrinology, 2004, vol. 2, No. 32, pp. 1-12.*
Kousta et al, "Successful Induction of Ovulation and Completed Pregnancy Using Recombinant Human Luteinizing Hormone and Follicle Stimulation Hormone in a Woman with Kallmann's Syndrome", Human Reproduction, 1996, pp. 70-71, col. 11, No. 1.
Deyo et al, "The Use of GnRH or LH to Synchronise Follicular Wave Emergence for Superstimulation in Cattle" Theriogenology, 2001, pp. 513, vol. 55.
Marco Filicori, M.D., "The Role of Luteinising Hormone in Folliculogenesis and Ovulation Induction", Fertility & Sterility, 1999, pp. 405-414, vol. 1999.
"Recombinant Human Luteinising Hormone is as Effective as, but Safer than, Urinary Human Chorionic Gonadotropin in Inducing Final Follicular Maturation and Ovulation in In Vitro Fertilization Procedures: Results of a Multicenter Double-Blind Study", J. Clin. Endocrinol. & Metabol., 2001, pp. 2607-2618, vol. 86.
David Lindsay Healy et al, "Female Infertility: Causes and Treatment", The Lancet, 1994, pp. 1539-1544, vol. 343.
Marco Filicori, "Gonadotropin-Releasing Hormone Analogs in Ovulation Induction: Current Status and Perspectives", Journal of Clinical Endocrinology and Metabolism, 1996, pp. 2413-2416, vol. 81.
Marco Filicori et al, "Different Gonadotropin and Leuprorelin Ovulation Induction Regimens Markedly Affect Follicular Fluid Hormone Levels and Folliculogenesis", Fertility and Sterility, Feb. 2, 1996, pp. 387-393, vol. 65.
M. Filicori et al, "Luteinizing Hormone Activity Supplementation Enhances Follicle-Stimulating Hormone Efficacy and Improves Ovulation Induction Outcome", The Journal of Clinical Endocrinology & Metabolism, 1999, pp. 2659-2663, vol. 84.
"Recombinant Human Luteinizing Hormone (LH) to Support Recombinate Human Follicle-Stimulating Hormone (FSH)-Induced Follicular Development in LH- and FSH-Deficient Anovulatory Women: A Dose-Finding Study", Journal of Clinical Endocrinology and Metabolism, 1998, pp. 1507-1514, vol. 83.
Michael W. Sullivan et al, "Ovarian Responses in Women to Recombinant Follicle-Stimulating Hormone and Luteinizing Hormone (LH): A Role for LH in the Final Stages of Follicular Maturation", Journal of Clinical Endocrinology and Metabolism, 1999, pp. 228-232,vol. 84.
E. Scott Sills et al, "A Prospective Randomized Comparison of Ovulation Induction Using Highly purified Follicle-Stimulating Hormone Alone and with Recombinant Human Luteinizing Hormone in In-Vitro Fertilization", Human Reproduction, 1999, pp. 2230-2235, vol. 14.

(Continued)

Primary Examiner—Christopher R. Tate
Assistant Examiner—Jennifer I Harle
(74) Attorney, Agent, or Firm—Browdy and Neimark, PLLC

(57) ABSTRACT

The invention provides a new use for LH, and analogues having LH-activity for aiding folliculogenesis in controlled ovarian hyperstimulation (COH), in which the LH or an analogue thereof is administered during a priming period lasting from day 1 to about day 4 of the stimulatory phase in COH.

9 Claims, No Drawings

OTHER PUBLICATIONS

Ben-Amor A-F, et al, "The Effect of Luteinizing Hormone Administered During Late Follicular Phase in Normo-Ovulatory Women Undergoing In-Vitro Fertilization", Human Reproduction, 2000, pp. 46, Abstract book 1, Abstract No. O-032.

L. Werlin et al, "A Multi-Center, Randomized, Comparative, Open-Label Trial to Assess the Safety and Efficacy of Gonal-F (r-hFSH) Versus Gonal-F and Recombinant Human Lutenizing Hormone (r-hLH) in Patients Undergoing ICSI: Preliminary Data", Fert. Steril., Sep. 1999, pp. S12, vol. 72, Abstract No. O-032.

R.S. Williams, "A Multi-Center Study Comparing the Efficacy of Recombinant Human Follicle Stimulating Hormone (r-hFSH, Gonal-F) Versus r-hFSH Plus Recombinant Human Luteinizing Hormone (r-hLH, Lhadi) in Patients Undergoing Controlled Ovarian Hyperstimulation (COH) for Assisted Reproductive Technologies (ART)", Fertil. Steril., 2000, pp. S228, vol. 74, Abstract No. p. 428.

H. Van Hell et al, "Effects of Human Menopausal Gonadotrophin Preparations in Different Bioassay Methods", Acta Endocrin, 1964, pp. 409-418, vol. 47.

Ludwig et al., Use of recombinant human chorionic gonadotropin in ovulation induction, Fertility and Sterility, 79(5) 1051-1059 (May 2001).

* cited by examiner

USE OF LH IN CONTROLLED OVARIAN HYPERSTIMULATION

FIELD OF INVENTION

The invention relates to the field of in vivo and in vitro assisted reproduction technologies (ART), specifically controlled ovarian hyperstimulation (COH) using gonadotropins.

BACKGROUND OF THE INVENTION

Numerous infertile patients undergo ovulation induction procedures every year. Up until two decades ago ovulation induction was used solely for the treatment of anovulatory infertility; however, the introduction of assisted reproduction technology (ART) has expanded the use of these procedures to eumenorrheic women, with the goal of achieving multiple folliculogenesis.

For assisted reproduction techniques (ART), such as in vitro fertilisation (IVF) or IVF in conjunction with intracytoplasmic sperm injection (IVF/ICSI) and embryo transfer (ET), oocytes are collected from a female patient immediately prior to ovulation. The oocytes are fertilised in vitro, the resulting embryos are evaluated, and selected for implantation. Fertilisation will not occur for every oocyte, and not every fertilised oocyte will develop into a viable embryo. Furthermore, implantation may fail to occur. Because of the many possibilities for an unsuccessful outcome, and the relatively invasive nature of oocyte collection, it is desirable to maximise the number of oocytes collected.

For this reason, ART is typically carried out using controlled ovarian hyperstimulation (COH) to increase the number of oocytes[1]. Standard regimens[2] for COH include a down-regulation phase in which endogenous luteinising hormone (LH) is down-regulated by administration of a gonadotropin releasing hormone (GnRH) agonist followed by a stimulatory phase in which follicular development (folliculogenesis) is induced by daily administration of follicle stimulating hormone (FSH), usually at about 150-225 IU/day. Other molecules having FSH activity may also be used. Alternatively stimulation is started with FSH after spontaneous or induced menstruation, followed by administration of a GnRH-antagonist (typically starting around day six of the stimulatory phase). When there are at least 3 follicles>16 mm (one of 18 mm), a single bolus of hCG (5-10,000 IU) is given to mimic the natural LH surge and trigger ovulation. Oocyte recovery is timed for 36-38 hours after the hCG injection.

The rationale for the use of GnRH analogues, e.g. agonists or antagonists, in this context is the prevention of an untimely LH surge which can cause premature ovulation and follicle luteinisation[3]. It has consistently been found that long GnRH agonist regimens (i.e., those started in the midluteal phase of the cycle preceding ovulation induction, or before) are associated with easier patient scheduling, greater follicle yield, and overall better clinical results.[4] The use of antagonists is relatively new to the clinic, but it is expected to yield similar benefits, with the advantage of a shorter dosing period.

The prolonged administration of GnRH agonists or the administration of GnRH antagonists results in profound suppression of endogenous LH throughout the cycle, in the case of an agonist, or late in the stimulatory phase, with an antagonist. This situation, while not incompatible with folliculogenesis, does not mimic the natural cycle. In the natural cycle, LH levels show a gradual increase several days before the large peak at midcycle.

Many groups have investigated the importance of LH during the stimulatory phase of COH and ovulation induction regimens. As is well known and recognised in the art, techniques or methods of ovulation induction (OI) are distinct from methods of COH, although both may involve the administration of FSH.

Filicori et al. has investigated the role of low doses of hCG, as a surrogate for LH, in folliculogenesis and ovulation induction[5]. hCG was given (50 IU hCG/day), starting synchronously with FSH administration. This regimen was continued on a daily basis until ovulation was triggered with a bolus of hCG. The numbers of small (<10 mm), medium (10-14 mm) and large (>14 mm) follicles were comparable between a group receiving hCG and a control group receiving FSH alone, however, the cumulative dose of FSH and the duration of FSH stimulation were reduced in the hCG treated group.

WO 00/67778 (Applied Research Systems) proposes the use of LH during the stimulatory phase. In one study, patients were administered FSH and LH in the early stimulatory phase, and then either both FSH and LH or just LH during the late stimulatory phase. In another study, patients were administered FSH alone in the early stimulatory phase and then LH in the late stimulatory phase. It was suggested that LH in the late stimulatory phase is responsible for atresia of non-dominant follicles. The regimen is proposed to encourage the development of a single dominant follicle.

The administration of rhLH (75 and 225 IU/day) for supporting rhFSH-induced follicular development in hypogonadotrophic hypogonadal women is reported by the *European Recombinant Human LH Study Group* to promote estradiol secretion, enhance the effect of FSH on follicular growth, and permit the successful luteinisation of follicles when exposed to hCG, as compared to a regimen of FSH alone[6]. The LH was administered starting on the same day as FSH stimulation, and was continued until hCG administration to trigger ovulation.

Sullivan et al. report that LH late in the stimulatory phase sustains follicular estradiol production when FSH is withdrawn[7].

Sills et al. report a study in which patients suffering from infertility of various types were treated with either FSH or FSH and 75 IU rhLH throughout the stimulatory phase. The authors conclude that the addition of exogenous LH throughout ovulation induction does not materially alter cycle performance[8].

Ben-Amor et al.[9] and Werlin et al.[10] have examined the effect of administering rhLH during the second half of the follicular phase in normally ovulatory patients with a long down regulation regimen, and Williams et al.[11] have studied the effect of administering different doses of r-hLH during the whole FSH stimulation. No substantial clinical benefits were reported in these patient groups.

In COH regimens using FSH, some patients ("poor responders") fail to respond to the initial doses of FSH, and the treatment cycle may be abandoned, and a new cycle started with a higher initial dose of FSH. Other groups of patients require repeated cycles because they fail to become pregnant even though oocyte recovery is successful. If repeat cycles are necessary, there may be adverse physical and emotional effects on the patient. Each repeat cycle entails a tremendous disruption in the life of the infertile couple.

It would be desirable to have a method that would permit the same or improved follicular response to COH using decreased FSH doses or decreased dosing periods. It would also be desirable to have a diagnostic test which could determine which patients may be poor or sub-optimal responders, and which patients may respond on a decreased FSH dose.

SUMMARY OF THE INVENTION

It is an object of the invention to provide an improved regimen for COH.

It is a further object of the invention to provide a method for providing multiple follicles for multiple oocyte recovery for ART.

It is a further object of the invention to provide a method for determining which patients may show a good, poor or sub-optimal response to FSH in COH.

In a first aspect, the invention provides the use of luteinising hormone (LH) or an analogue thereof, for the manufacture of a medicament for inducing multiple folliculogenesis in a human patient, wherein the medicament is to be administered from day 1 to at or about day 4 of the stimulatory phase in COH.

Viewed alternatively, the invention provides the use of luteinising hormone (LH) or an analogue thereof, for the manufacture of a medicament for inducing multiple folliculogenesis in a human patient, wherein the medicament is to be administered during a priming period lasting from day 1 to at or about day 4 of the stimulatory phase in COH.

In a second aspect, the invention provides the use of luteinising hormone (LH) or an analogue thereof, for inducing multiple folliculogenesis in a human patient, wherein the LH is to be administered from day 1 to at or about day 4 of the stimulatory phase in COH.

Viewed alternatively, the invention provides the use of luteinising hormone (LH) or an analogue thereof, for inducing multiple folliculogenesis in a human patient, wherein the LH is to be administered during a priming period lasting from day 1 to at or about day 4 of the stimulatory phase of COH.

In a third aspect, the invention provides a pharmaceutical composition comprising LH or an analogue thereof, at a daily dose of 20-400 IU LH, to be administered from day 1 to at or about day 4 of the stimulatory phase in COH.

Preferably the medicament or pharmaceutical composition (comprising LH or an analogue thereof) is to be administered from day 1 to day 4, preferably from day 1 to day 3 or most preferably from day 1 to day 2 of the stimulatory phase. Single daily doses of medicament or pharmaceutical compositions may be administered. Alternatively the medicament or pharmaceutical composition may be administered as a single dose on day 1 of the stimulatory phase. Preferably the pharmaceutical compositions of the invention are designed for use in the methods and uses of the invention.

In a fourth aspect, the invention provides a kit for the induction of folliculogenesis in a human patient, the kit comprising one to five daily doses of 20-400 IU of LH, or an equivalent dose of an analogue thereof, and at or about six or more daily doses of FSH, or an analogue thereof. Thus, the kits of the invention may comprise or consist of one, two, three, four or five daily doses of LH, or an analogue thereof, and at or about six or more daily doses of FSH, or an analogue thereof. Appropriate daily doses of LH and FSH are described elsewhere herein. Preferred kits may comprise two, three or four daily doses of at or about 150 IU of LH or 225 IU of LH and eight to twelve daily doses of at or about 150 IU FSH. Preferably the kits of the invention are designed for use in the methods and uses of the invention.

In a fifth aspect, the invention provides a method for determining the response of a patient to FSH in COH, the method comprising the steps:

(A) measuring androgen concentration in the patient to yield a basal value $A^1$;

(B) administering LH at about 20 to about 400 IU to the patient;

(C) measuring androgen concentration in the patient at least once after administering LH, at or about 6 or more hours, or preferably at or about 12 or more hours, after administering LH, to yield a value $A^2$;

(D) classifying the patient as a poor, sub-optimal or good responder on the basis of the change in androgen levels.

Alternatively, as will be described in more detail below, in step (C) of the above method androgen levels/concentrations may be monitored/measured at least once over a period of time after the LH administration, and one or more of these measurements of androgen levels may be taken within the first six hours after the administration of LH, e.g. after 1 hour, and then subsequent measurements may be taken at one or more later time points, to yield a value $A^2$. Generally the measurements are taken over a period of 24 hours after LH administration.

In a sixth aspect, the invention provides a method for determining the response of a patient to FSH in COH, the method comprising the steps:

(A) measuring oestrogen concentration in the patient to yield a basal value $E^1$;

(B) administering LH at about 20 to about 400 IU, to the patient;

(C) administering FSH at about 5 to about 300 IU to the patient, at or about 6 or more hours, or preferably at or about 12 or more hours, more preferably at or about 24 or more hours after administering LH;

(D) measuring oestrogen concentration in the patient, at or about 12 or more hours after administering FSH, to yield the value $E^2$;

(E) classifying the patient as a poor, sub-optimal or good responder on the basis of the change in oestrogen levels $(E^2-E^1)$.

Alternatively as will be described in more detail below, in step (D) of the above method oestrogen levels/concentrations may be monitored/measured at least one over a period of time after the FSH administration, and one or more of these measurements of oestrogen levels may be taken within the first twelve hours after the administration of FSH, e.g. after 6 hours, and then subsequent measurements may be taken at one or more later time points, to yield a value $E^2$.

In all the above described methods for determination, the measurements of oestrogen and androgen levels are preferably carried out in vitro on a sample taken from an appropriate patient.

A further aspect of the invention provides LH or an analogue thereof for inducing multiple folliculogenesis in a human patient, wherein the LH, or an analogue thereof is to be administered from day 1 to at or about day 4 of the stimulatory phase in COH.

A further aspect of the invention provides LH or an analogue thereof for inducing multiple folliculogenesis in a human patient, wherein the LH, or an analogue thereof, is to be administered during a priming period lasting from day 1 to at or about day 4 of the stimulatory phase in COH.

In a yet further aspect, the present invention provides a method of inducing multiple folliculogenesis in a patient, which method comprises the administration of LH or an analogue thereof to the patient, wherein said administration is carried out from day 1 to at or about day 4 of the stimulatory phase in COH.

In a further aspect, the present invention provides a method of inducing multiple folliculogenesis in a patient, which method comprises the administration of LH or an analogue thereof to the patient, wherein said administration is carried out during a priming period lasting from day 1 to at or about day 4 of the stimulatory phase in COH.

DETAILED DESCRIPTION OF THE INVENTION

The present invention relates to the administration of LH (or an analogue thereof in order to induce multiple folliculogenesis or otherwise improve COH regimens in a human patient, in terms of for example increasing the number of retrieved embryos which show early cleavage and thereby have a higher chance of implantation and pregnancy, an increase in the number of follicles of over 15 mm on the day of ovulation triggering, a higher ratio of large follicles to small follicles on the day of ovulation triggering and a greater number of oocytes. Thus, the invention can also be viewed as providing improved COH regimens which result in increased or improved implantation and/or pregnancy rates in a human patient, for example compared to a patient or group of patients undergoing conventional COH regimens.

It has surprisingly been found that the administration of a comparatively short regimen of LH starting at the beginning of the stimulatory phase, and followed by FSH administration in a COH treatment has the effect of enhancing multiple folliculogenesis and generally improving the COH regimen in terms of for example increasing the number of retrieved embryos which show early cleavage and thereby have a higher chance of implantation and pregnancy, an increase in the number of follicles of over 15 mm on the day of ovulation triggering, a higher ratio of large follicles to small follicles on the day of ovulation triggering and a greater number of oocytes. Moreover, it is possible to decrease the dose of FSH that is required to achieve multiple follicular development in a patient. The technique has been called "LH priming".

The period in which LH is administered is termed the priming period. For the purposes of this description, the beginning of the priming period defines the beginning of the stimulatory phase.

It is believed that LH interacts with receptors on theca cells of the developing follicle, stimulating the production of androgens. Oestrogen synthesis requires the availability of androgens as aromatase substrates.

It is believed that the increased local concentration of androgens induced by LH enhances the action of FSH on the growing follicle.

Where LH is used or administered in the aspects of the invention described herein the dosage may be in the range of from at or about 20 to at or about 400 IU, preferably from at or about 5 to at or about 300 IU or from at or about 75 IU to at or about 225 IU, more preferably from at or about 100 IU to at about 200 IU or from at or about 75 IU to at or about 150 IU LH, most preferably at or about 150 IU. Alternative dosages may be from at or about 150 IU to at or about 300 IU LH, preferably at or about 225 IU LH. Preferably these doses are daily doses. If an LH analogue is used, the equivalent to these LH doses can be calculated and administered.

Where FSH is used or administered in the aspects of the invention described herein the dosage may be in the range of from at or about 50 to at or about 300 IU, preferably from at or about 100 to at or about 250 IU, most preferably at or about 150 IU. Alternative doses of FSH may be at or about 75-600 IU, 75-450 IU, preferably at or about 150-375 IU, more preferably at or about 300 IU. Preferably these doses are daily doses. If an FSH analogue is used, the equivalent to these doses can be calculated and administered.

In a preferred protocol, a GnRH agonist is administered to the patient, in a dosage sufficient to attain suppression of ovarian function. Appropriate methods to obtain such suppression are well known and documented in the art and any of these can be used, for example, a single injection of 3.75 mg of depot Triptorelin, or daily doses of Buserelin or leuprolide acetate can be used. Suppression of ovarian function may be monitored by monitoring LH or estradiol levels (LH<5 IU/L, $E_2$<50 pg/ml generally indicate quiescence). The stimulatory phase can be started with daily injections of LH (for example at the doses described above, e.g. about 20-400 IU, and preferably at 150 IU or 225 IU). After about 3 to 4 days, for example after 2.5 days, 3 days, 3.5 days, 4 days or 4.5 days, LH administration is ceased and FSH is given (for example at the doses described above, usually about 50-300 IU/day). FSH administration is generally continued until ultrasound imaging reveals at least 3 follicles>16 mm (one of 17 mm or 18 mm or more). Ovulation is triggered with a bolus of hCG (5'000-10'000 IU). In an alternative preferred protocol FSH and LH administration can overlap by one day, i.e. FSH can be administered on the last day of LH administration.

A single administration of LH or an analogue thereof may suffice, and FSH administration may be commenced simultaneously, or preferably, the following day. When a single dose of LH is administered, it should preferably be about 20-400 IU LH. Alternatively, LH may be administered for up to a total of four days, e.g. the LH (or analogue) may be administered from day 1 up to at or about day 4 or from day 1 up to at or about day 3 or from day 1 up to at or about day 2. In such cases preferably the LH is administered on a daily or semi-daily basis, for example at the doses described above. FSH administration may be started simultaneously with LH administration, or may overlap for three, two or one day, but preferably begins after LH administration has ceased or with only one day of overlap. In other words, in preferred embodiments LH is administered in the absence of administration of exogenous FSH in the priming period. Preferred doses of FSH and LH in this regard are again described above.

The daily doses need not be equal. For example, in a preferred regimen, on day 1 a dose of 150-300, preferably 225 IU LH may be given, on day 2, a dose of 75-225, preferably 150 IU LH may be given, and on days 3 and 4, doses of 75-225, preferably 75-150 IU LH may be given. Alternatively, the daily doses may be equal and in an alternative preferred regimen daily doses of 225 IU LH may be given.

The preferred routes for gonadotropin administration are well known and documented in the art and are by subcutaneous, intramuscular or intravenous injection. Analogues may be administered by subcutaneous, intramuscular or intravenous injection, or orally, transdermally, rectally or intranasally as appropriate for the analogue in question.

An LH priming regimen may also be used in conjunction with treatment with a GnRH antagonist rather than a GnRH agonist. The stimulatory phase is started by administration of LH (as described above) in the late luteal phase of the previous cycle (preferably days 23-26, or about three days prior to the anticipated start of menses). Then FSH is given, as above, starting on day 1-3 of menstruation (without previous administration of a GnRH agonist). Then, on about FSH stimulation day 6, a GnRH antagonist is administered, for example Antide, Azaline B, Cetrorelix, Ganirelix or Antarelix. Ovulation is triggered with a bolus of hCG. Usually the antagonist is administered until the day of hCG administration. Preferably LH and FSH administration do not substantially overlap, for example it is preferred that they overlap for not more than three days, more preferably not more than two days and most preferably not more than one day. More preferably FSH administration begins after LH administration has ceased, i.e. there is no overlap.

In order to better predict the start of menses, it may be desirable to administer a contraceptive pill to the patient for about one month, prior to starting the LH priming regimen. Withdrawal of the contraceptive is usually followed by menses about two or three days later. If a contraceptive pill is used, LH priming may be started on the day that the pill is withdrawn.

Ultrasound imaging may be used throughout the stimulatory phase to monitor the development of follicles.

The use of LH in the early stimulatory phase of a COH regimen can permit the reduction of total FSH dose that is used, as compared to a COH regimen without LH. For example, the usual dose of FSH that is used without previous LH administration, is in the range of 100-250 IU/day, usually about 150 IU/day. With LH priming, if follicular response is judged sufficient, the FSH dose may be reduced to for example a dose of less than 150 IU/day, or less than 100 IU/day, for example a dose of 50-140 IU/day or 50-90 IU/day. Alternatively the same or lower daily dose may be used, and ovulation triggered earlier than is the case without LH priming, meaning that the cumulative FSH dose is less.

The invention has been described with respect to luteinising hormone (LH), however, one skilled in the art will understand that compounds having LH activity i.e. LH analogues which exert the same physiological, biochemical or biological effects as LH may also be used. For example, it is well known that chorionic gonadotropin (CG) can serve as a surrogate for LH. As a general rule 1 IU of hCG is equivalent to 5-7 IU of LH in the pharmacopoeia Van Hell bioassay[12] and thus equivalent doses of hCG can be calculated by a person skilled in the art.

Other examples of analogues of LH are as disclosed, for example in European patent no. EP 0 322 226 (Applied Research Systems), WO 99/25849, WO 90/06844, WO 93/06844 and WO 96/05224 (all to Washington University), and WO 00/61586 (Akzo Nobel).

The invention has been discussed in the context of FSH as the major follicular stimulating agent. It will be understood by one of skill in the art that FSH may be substituted by a biologically active analogue, or by a compound that stimulates endogenous FSH secretion. In this latter class are included aromatase inhibitors, and anti-oestrogens such as tamoxifen and clomiphene citrate (CC). These compounds stimulate endogenous FSH secretion by removing the negative feedback exerted by oestrogen on the hypothalamus (either by antagonising oestrogen receptors, as is the case with CC and tamoxifen, or by greatly decreasing oestrogen concentrations, as is the case with aromatase inhibitors). FSH may also be used in conjunction with these agents during the stimulatory phase.

A particularly preferred form of FSH for use in conjunction with the use of LH according to the invention is known as FSH-CTP. This long-acting human FSH is described in WO 93/06844, and has a wild type FSH α-subunit and a β-subunit that consists of the wild type FSH β-subunit fused at its carboxyl terminal to the carboxy terminal peptide (CTP) of the β-subunit of hCG (residues 112-118 to position 145 of the native hCGβ sequence). Other types of FSH analogues include, for example single chain FSH analogues in which the β-subunit is fused to the CTP of hCG, which in turn is fused to FSH α-subunit, as described in WO 96/05224 (single chain FSH-CTP). FSH may also be used in conjunction with these agents during the stimulatory phase.

Administration of LH preferably begins on day 1 of the stimulatory phase, and does not continue beyond day 4. If a patient is judged to be a good responder, daily doses of about 20-400 IU of LH on days 1 and 2 may suffice. If a patient is judged to be a poor or sub-optimal responder, daily doses of 20-400 IU LH may be continued and stopped on any one of days 3 or 4. The determination of whether a patient is a good, sub-optimal or poor responder may be based on results in previous ART cycles, or on the results of a diagnostic test, as described below.

As mentioned previously, hCG exerts many of the same biological effects as LH. hCG has a considerably longer half-life than LH, so if hCG is used instead of LH, a single administration of hCG (about 3-100 IU hCG) on day 1 may suffice.

As mentioned above, in a further aspect, the invention provides a method for determining the response of a patient to FSH in COH. This allows the tailoring of the COH regimen to the patient, avoiding excessive doses of FSH in good responders and increasing the chances of success for sub-optimal and poor responders. The method uses a single administration, e.g. injection of LH (for example at the doses described above, e.g. about 50-300 IU, preferably 100-200 IU, more preferably about 150 IU) at the beginning of the stimulatory phase of a COH regimen, as a "challenge" in order to stimulate androgen synthesis by theca cells. The LH injection is made on day 1 of the stimulatory phase. Serum androgen levels are then measured at least once, at least at or about 6 hours after LH administration, preferably at least at or about 12 hours after LH administration. Before 6 hours, the response to the LH challenge will not be significant. More preferably, androgen levels are monitored, over a period of time, for example, at 0, 1, 6, 12 and 24 hours after the LH injection, giving a picture of the increase in androgen concentrations in response to the LH injection. Androgen levels after the LH challenge are compared with levels prior to the challenge. For example, if the androgen level prior to the LH injection is $A^1$ and the androgen level post injection is $A^2$, the difference between these two values, $\Delta A$, is calculated (i.e. $\Delta A = A^2 - A^1$). The value $\Delta A$ is intended to represent a general parameter representing a change in androgen serum levels. It is not limited to a simple difference calculated from two values, but can also be a composite result from a number of points.

If a single measurement of androgen levels is made, it should not be made before about 6 hours, as androgen levels will not have time to respond to the LH challenge. If a single measurement is made, it is preferably made after 12 hours, more preferably at or about 18 to at or about 24 hours.

The LH challenge method is preferably used in patients undergoing a pituitary down-regulation regimen, involving a treatment of at least about 3 days, preferably about 7 days, with a GnRH agonist before LH administration.

Patients showing a good androgen response may continue the COH regimen with FSH alone. Patients showing a poor or sub-optimal response may receive LH injections (e.g. at the dosages described above, e.g. 50-300 IU, preferably 75-225 IU, more preferably about 150 IU/day) for up to about three days more, for example the patient would receive injections for 1, 2 or 3 days more, for example until a good androgen response is seen. Then FSH is administered daily, at about 75-600 or 75-450 IU/day, preferably about 150-375 IU/day, more preferably at about 300 IU/day.

The androgens which are preferably monitored are androstenedione and testosterone, more preferably androstenedione. In addition, precursors to these may be measured, for example 17-α-hydoxyprogesterone (17αOHP).

Good responders are those patients showing an increase in serum androstenedione concentration (ΔA) after 24 hours of at or about 2 nmol/L or more. Poor and sub-optimal responders show an increase less than at or about 2 nmol/L. If testosterone concentrations are measured, a good responder will show an increase in testosterone serum levels after 24 hours of at or about 0.25 to 0.75 nmol/L or more, whereas poor and sub-optimal responders show an increase of less than 0.25 nmol/L.

Patients which show a good, poor or sub-optimal androgen response, respectively, leads to the patients in turn being determined as likely to show a good, poor or sub-optimal response, respectively, to FSH in COH. Thus, for example a patient which shows a good androgen response leads to the patient being determined as likely to show a good response to FSH in COH in the methods of the invention described herein.

To increase the sensitivity of the method, background levels of androgen may be essentially eliminated by administering to the patient an inhibitor of adrenal androgen secretion, for example dexamethasone, prior to the LH challenge.

In a variation of the above LH challenge, serum oestrogen levels are monitored rather than androgen levels. LH stimulates production of androgens by theca cells, and androgens are then converted to oestrogens by aromatase.

Because conversion of androgens to estrogens is enhanced by FSH, in a further variation of the LH challenge method, the LH challenge may be followed by an FSH injection, and oestrogen levels may then be measured. Again, a single injection of LH (e.g. at the dosages described above, e.g. about 50-300 IU, preferably 75-225 IU, more preferably about 150 IU) is given on day 1 of the stimulatory phase of a COH regimen, as a "challenge" in order to stimulate androgen synthesis by theca cells. Following the LH injection, an FSH injection is given (about 50-300 IU, preferably about 150 IU). The FSH injection is given not before at or about 6 hours, preferably at or about 12 hours, more preferably at or about 24 hours after the LH challenge. FSH stimulates aromatase production, thus the increase of androgen that is caused by LH stimulation of theca cells, will be converted by aromatase into oestrogens. Oestrogen levels are then measured at least once, preferably not before at or about 12 hours after FSH administration. The 12-hour interval allows aromatase upregulation to occur in response to FSH. More preferably, oestrogen levels are monitored, over a period of time, for example, at 0, 6, 12 and 24 hours after the FSH injection. Oestrogen levels after the LH challenge are compared with levels prior to the challenge. For example, if the oestrogen level prior to the LH injection is $E^1$ and the oestrogen level post injection is $E^2$, the difference between these two values, ΔE, is calculated (i.e. $\Delta E = E^2 - E^1$). The value ΔE is intended to represent a general parameter representing a change in oestrogen serum levels. It is not limited to a simple difference calculated from two values, but can also be a composite result from a number of points.

If a single measurement of oestrogen levels is made, it should not be made before about 12 hours after the FSH challenge injection, as oestrogen levels will not have time to respond to the LH/FSH challenge. If a single measurement is made, it is preferably made after 18 hours, more preferably at or about 24 hours.

The LH+FSH challenge method is preferably used in patients undergoing a pituitary down-regulation regimen, involving a treatment of at least about 3 days, preferably about 7 days, with a GnRH agonist before LH administration.

Patients showing a good oestrogen response may continue the COH regimen with FSH alone (about 100-225 FSH IU/day, preferably about 150 IU FSH/day). Patients showing a poor or sub-optimal response may continue LH injections (e.g. at the doses described above, e.g. 50-300 IU, preferably 75-225 IU, more preferably about 150 IU/day) for up to about three days more, for example the patient would receive injections for 1, 2 or 3 days more, for example until a good oestrogen response is seen, then FSH doses are started (e.g. at the doses described above or e.g. about 75-450 IU FSH/day, preferably about 150-375 IU/day, more preferably about 300 IU/day).

The oestrogen that is preferably monitored is estradiol ($E_2$).

Good responders are those patients showing an increase of oestradiol serum levels after 24 hours of at or about 50 pmol/L or more. Poor and sub-optimal responders show a response less than this.

Patients which show a good, poor or sub-optimal oestrogen response, respectively, leads to the patients in turn being determined as likely to show a good, poor or sub-optimal response, respectively, to FSH in COH. Thus, for example a patient which shows a good oestrogen response leads to the patient being determined as likely to show a good response to FSH in COH in the methods of the invention described herein.

To increase the sensitivity of the method, background levels of androgen may be essentially eliminated by administering to the patient an inhibitor of adrenal androgen secretion, for example dexamethasone, prior to the LH challenge.

Any of the above challenges may be repeated, during the course of the stimulatory phase.

In any of the above challenges, both androgens and oestrogens are preferably monitored. Methods of monitoring androgens and oestrogens are well known and documented in the art and any of these may be used.

Testosterone levels may be measured, using for example, a solid-phase coated-tube radioimmunoassay (Coat-A-Count™, Diagnostic Products Corporation, Los Angeles, USA).

Androstenedione levels may be measured, for example using radioimmunoassay (Diagnostic Laboratories Inc., Webster, USA).

17β-estradiol may be measured, for example, by radioimmunoassay (Diagnostic Products Corporation, Los Angeles, USA).

The gonadotropins that are used in the methods and uses of the invention should preferably be human gonadotropins and may be from any source, provided they are not contaminated with any materials (particularly other gonadotropins) which will substantially affect their action. Urinary gonadotropins may be used, although it is preferred to use recombinant FSH and LH (rhFSH and rhLH), because of their high purity. It is particularly preferred to use rhLH.

The pharmaco-kinetics of rhLH are very similar to those of pituitary LH. Following a rapid distribution phase with an initial $t_{1/2}$ of 1 h, rhLH is eliminated with a terminal $t_{1/2}$ of approximately 10 h. Total body clearance is 2 L/h, with less than 5% of the dose being excreted renally. The steady state volume is 8 L. These PK characteristics contrast with urine-derived hCG PK characteristics. The latter have been shown to have a terminal $t_{1/2}$ exceeding 30 hours. hCG is expected to remain in circulation 2 to 3 times longer than LH.

Pharmaceutical compositions comprising LH or an analogue thereof and a pharmaceutically acceptable diluent, carrier or excipient, for use in the method of the invention, e.g. for inducing or enhancing folliculogenesis are also within the scope of the present invention. A person skilled in the art is aware of a whole variety of such diluents or excipients suitable to formulate a pharmaceutical composition. Preferably said pharmaceutical compositions comprise a daily dose of LH (e.g. a dose of 20-400 IU, preferably 50-300 IU, more preferably 75-225 IU or 100-200 IU or most preferably 150 IU of LH) to be administered from day 1 to about day 4, preferably from day 1 to day 4, more preferably from day 1 to day 3, most preferably from day 1 to day 2 or only on day 1 of the stimulatory phase in COH. Other appropriate doses of LH are described elsewhere herein.

LH is typically formulated as a unit dosage in the form of a solid ready for dissolution to form a sterile injectable solution for intramuscular or subcutaneous use. The solid usually results from lyophilisation. Typical excipients and carriers include sucrose, lactose, sodium chloride, buffering agents like sodium phosphate monobasic and sodium phosphate dibasic. The solution may be prepared by diluting with water for injection immediately prior to use.

LH may also be formulated as a solution for injection, comprising any of the excipients and buffers listed above, and others known to one skilled in the art.

Small molecule LH agonists, such as those reported in WO 00/61586 (Akzo Nobel) may be given orally, in the form of a syrup, tablet or capsule, after admixing with a suitable excipient. Alternatively, they may be given intranasally, in the form of a solution or fine powder suitable for spraying.

The invention will now be described in more detail in the following non-limiting Example.

EXAMPLE

Patients are selected as follows:

Inclusion Criteria
  Type of infertility: Tubal IVF and unexplained infertility. (n=120 in total)
  Normal menstrual rhythm
  Aged <37 years
  Body mass index (BMI) ≦30
  No recent hormone administration
  2 functional ovaries Exclusion Criteria
  Ultrasound determination of PCO
  BMI>30
  Single functional ovary
  Other compromising disease Protocol
  Patients are down-regulated (starting on day 18-23 of a menstrual cycle) with injections of Lupron®, Synarel® or Zoladex® for 14-18 days prior to start. The start point for the priming period (day L1) requires oestradiol ($E_2$) serum levels of <150 pmol/L (50 pg/ml) and no more than one ovarian cyst with diameter <30 mm.

On days L1-L4 (the priming period), the patients receive placebo, or 225 IU rhLH daily.

Starting on the last day of the priming period, the patients receive 150 IU FSH daily (LH administration ceases after L4), for 7 days (S1 to S7). Doses may be reduced at S7 or later, if there is risk of over-stimulation. At S7, doses are increased to 300 IU FSH/day if the circulating concentration of $E_2$ is less than 450 pmol /L, and/or there are <6 follicles with diameter >8 mm.

FSH administration is continued until the largest follicle has reached a mean diameter of at least 17 mm, and there are two other follicles with a mean diameter of ≧16 mm, at which point an ovulation triggering dose of hCG (5'000-10'000 IU hCG) is administered. Oocyte retrieval is timed for approximately 36 hours after the hCG injection. Oocytes are fertilised in vitro. Embryos that show early cleavage (by 25 hours after insemination) are considered to have considerably higher chances of implantation and pregnancy. The early cleavage (EC) check is carried out at 25 h after insemination, and the number of cleaved embryos, syngamy (merging of the sperm and the ova) and non-cleaved embryos recorded.

Also recorded are:
Number and diameter of follicles on day of hCG, and in particular the number of follicles over 15 mm in diameter;
oocyte yield;
ampoules of rFSH used;
ampoules of rFSH used per oocyte;
circulating concentration of oestradiol on S7;
reduction in the incidence of 'poor responses' to standard dose therapy (150 IU FSH/d) in a clinic population;
Ratio of large follicles to small follicles at the time of hCG administration;
the number of follicles with mean diameter >10 mm at S7;
circulating inhibin-B concentrations at S7.

REFERENCES

[1] Healy et al.; *Lancet* 343 1994; 1539-1544
[2] for example, a conventional technique is described in EP 0 170 502 (Serono Laboratories, Inc.)
[3] Filicori, M.; *J. Clin. Endocrinol. Metab.* 81 1996; 24136
[4] Filicori, M. et al.; *Fertil. Steril.* 65 1996; 387-93
[5] Filicori et al.; *J. Clin. Endocrnol. Metab.* 84 1999; 2659-2663
[6] The European Recombinant Human LH Study Group; *J. Clin. Endocrinol. Metab.* 83 1998; 1507-1514
[7] Sullivan, M. W. et al.; *J. Clin. Endocrinol. Metab.* 84 1999; 228-232
[8] Sills et al.; *Human Reproduction* 14 1999; 2230-2235
[9] Ben-Amor A-F, on behalf of the Study Group (Tarlatzis B, Tavmergen E, Shoham Z, Szamatowicz M, Barash A, Amit A, Levitas I, and Geva E). The effect of luteinizing hormone administered during late follicular phase in normo-ovulatory women undergoing in vitro fertilization. Hum Reprod 2000;15 (Abstract book 1):46 (Abstract no. 0-116).
[10] Werlin L., Kelly, E, Weathersbee P., Nebiolo L., Ferrande L. A multi-center, randomized, comparative, open-trial to assess the safety and efficacy of Gonal-F (r-hFSH) versus Gonal-F and recombinant human luteinizing hormone (r-hLH) in patients undergoing ICSI: Preliminary data. . Fertil. Steril. 1999 72;3 (Suppl 1)(Abstract no. O-032).

[11] Williams R. S., A multi-center study comparing the efficacy of recombinant human FSH (Gonal-F) versus r-hFSH plus recombinant human LH in patients undergoing Controlled Ovarian Hyperstimulation for Assisted Reproductive Technology. Fertil. Steril. 2000, 74;3 (Suppl 1)(Abstract no. P-428)

[12] Van Hell et al.; *Acta Endocrin,* 47 1964; 409-418

The invention claimed is:

1. A method for inducing multiple folliculogenesis in a human patient, comprising administering luteinising hormone (LH) during a priming period beginning on day 1 of the stimulatory phase in controlled ovarian hyperstimulation (COH) and not continuing beyond day 4 of the stimulatory phase in COH.

2. The method according to claim 1, wherein the medicament is administered in the absence of administration of exogenous FSH in the priming period.

3. The method according to claim 1, wherein the medicament is administered at a dosage of about 20-400 IU LH/day, about 100-200 IU LH/day or about 150 IU LH/day.

4. The method according to claim 1, wherein the priming period lasts from day 1 to day 3 of the stimulatory phase.

5. The method according to claim 1, wherein the priming period lasts from day 1 to day 2 of the stimulatory phase.

6. The method according to claim 1, wherein the medication is to be administered as a single dose on day 1 of the stimulatory phase.

7. The method according to claim 1, wherein the LH is rhLH.

8. A method for inducing multiple folliculogenesis in a human patient, comprising administering human chorionic gonadotropin (hCG), during a priming period beginning on day 1 of the stimulatory phase of controlled ovarian hyperstimulation (COH) and not continuing beyond day 4 of the stimulatory phase of COH.

9. The method according to claim 8, wherein the hCG is administered in the absence of administration of exogenous FSH in the priming period.

* * * * *